(12) United States Patent
Yngve

(10) Patent No.: US 9,464,980 B2
(45) Date of Patent: Oct. 11, 2016

(54) TURF TESTING APPARATUS AND METHODS

(76) Inventor: Paul W Yngve, Lewes, DE (US)

( * ) Notice: Subject to any disclaimer, the term of this patent is extended or adjusted under 35 U.S.C. 154(b) by 0 days.

(21) Appl. No.: 13/479,565

(22) Filed: May 24, 2012

(65) Prior Publication Data
US 2012/0297889 A1 Nov. 29, 2012

Related U.S. Application Data

(60) Provisional application No. 61/489,868, filed on May 25, 2011.

(51) Int. Cl.
*G01N 3/08* (2006.01)
*G01N 19/02* (2006.01)

(52) U.S. Cl.
CPC ..................... *G01N 19/02* (2013.01)

(58) Field of Classification Search
CPC .......... G01N 3/08; G01N 3/34; G01N 19/02; G01N 3/56; G01M 19/00
USPC ....................................................... 73/9, 818
See application file for complete search history.

(56) References Cited

U.S. PATENT DOCUMENTS

| | | | |
|---|---|---|---|
| 3,975,940 A * | 8/1976 | Brungraber | 73/9 |
| 4,081,989 A * | 4/1978 | Majcherczyk | 73/9 |
| 5,195,357 A | 3/1993 | Takino et al. | |
| 5,259,236 A * | 11/1993 | English | 73/9 |
| 6,854,316 B2 * | 2/2005 | Hage et al. | 73/9 |
| 7,290,436 B2 * | 11/2007 | Olde Weghuis et al. | 73/9 |
| 8,146,402 B2 * | 4/2012 | Collins et al. | 73/9 |

FOREIGN PATENT DOCUMENTS

| | | |
|---|---|---|
| DE | 3808454 | 1/1989 |
| JP | 57125832 | 8/1982 |
| JP | 02021240 | 1/1990 |
| WO | WO9835218 | 8/1998 |

OTHER PUBLICATIONS

International Search Report mailed on Sep. 8, 2012, for PCT/US2012/039370.
International Preliminary Report on Patentability mailed on Dec. 5, 2013, for PCT/US2012/039370.

* cited by examiner

*Primary Examiner* — Lisa Caputo
*Assistant Examiner* — Octavia Hollington
(74) *Attorney, Agent, or Firm* — Robinson IP Law, PLLC

(57) ABSTRACT

Improved apparatuses and methods for testing turf or other surfaces, in one embodiment, a turf testing apparatus includes two actuators for moving a shoe relative to a turf surface. The first actuator moves the shoe along a substantially horizontal axis and the second actuator moves the shoe along a substantially vertical axis.

22 Claims, 6 Drawing Sheets

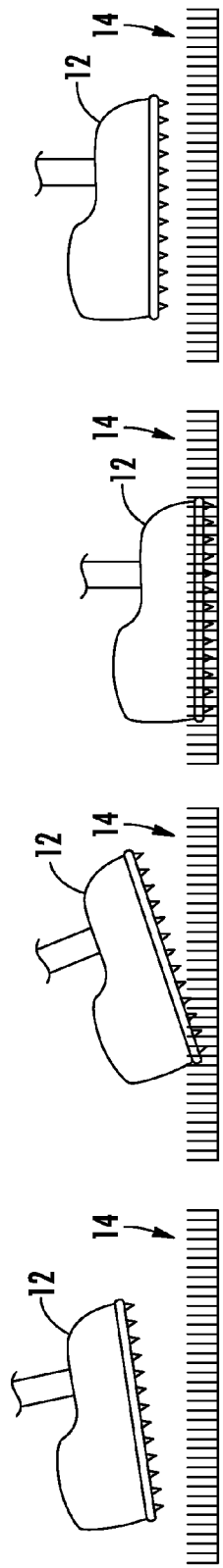

TURF TESTING APPARATUS AND METHODS

RELATED APPLICATIONS

This application claims the benefit of U.S. Ser. No. 61/489,868 filed May 25, 2011 titled "Turf Testing Apparatus and Methods," the entire contents of which are hereby incorporated by reference.

RELATED FIELDS

Apparatuses and methods for testing turf surfaces, including natural grass and artificial turf surfaces, as well as for testing shoes and other structures that interface with a turf surface.

BACKGROUND

Turf surfaces, including natural grass and artificial turf, are commonly used for sports and other physical activities. Properties of these surfaces, such as friction and traction, vary widely among different turf surfaces and can affect the suitability of a particular turf for particular activities, and may also correlate with the occurrence of injuries on that surface. Similarly, friction, traction and other properties of shoes, other footwear, and other structures used on such surfaces can also vary widely.

There are several devices currently available to measure friction and traction forces at a shoe/turf interface; however, many of the available devices are undesirable.

SUMMARY

Embodiments of the invention provide improved apparatuses and methods for testing turf or other surfaces and footwear or other structures that interact with such surfaces, including evaluating forces, such as, but not limited to, friction and traction forces acting at the footwear/turf interface.

In one embodiment, a turf testing apparatus includes two actuators for moving a shoe relative to a turf surface. The first actuator moves the shoe along a substantially horizontal axis and the second actuator moves the shoe along a substantially vertical axis. The apparatus also includes a pivot that allows the shoe to rotate relative to the turf surface.

In one embodiment of using the turf testing apparatus described in the previous paragraph, the first actuator first moves the shoe along a substantially horizontal axis without the shoe being in contact with the turf surface. As the first actuator is moving the shoe along the horizontal axis, the second actuator moves the shoe along a substantially vertical axis such that the shoe comes into contact with the turf surface. The first actuator continues to attempt to move the shoe along the substantially horizontal axis after the second actuator has moved the shoe into contact with the turf surface, and the pivot allows the shoe to pivot relative to the turf surface during this time. Subsequently, the second actuator moves the shoe along the substantially vertical axis to move the shoe away from the turf surface.

In the afore-described embodiment, force sensors measure forces along the horizontal and vertical axes during at least portions of the movement of the shoe. These force measurements may be used to study the force environments during impact and at other times during the shoe/turf surface interface, and may allow one to reach conclusions about the suitability of a particular turf surface or shoe, or to compare and contrast a turf surface and/or shoe with other turf surfaces and shoes in order to test and/or improve the same.

BRIEF DESCRIPTION OF FIGURES

FIGS. 3A-D illustrate an impaction and release cycle of a shoe relative to a turf surface using the turf testing apparatus of FIG. 1.

DETAILED DESCRIPTION OF FIGURES

Figure 1:
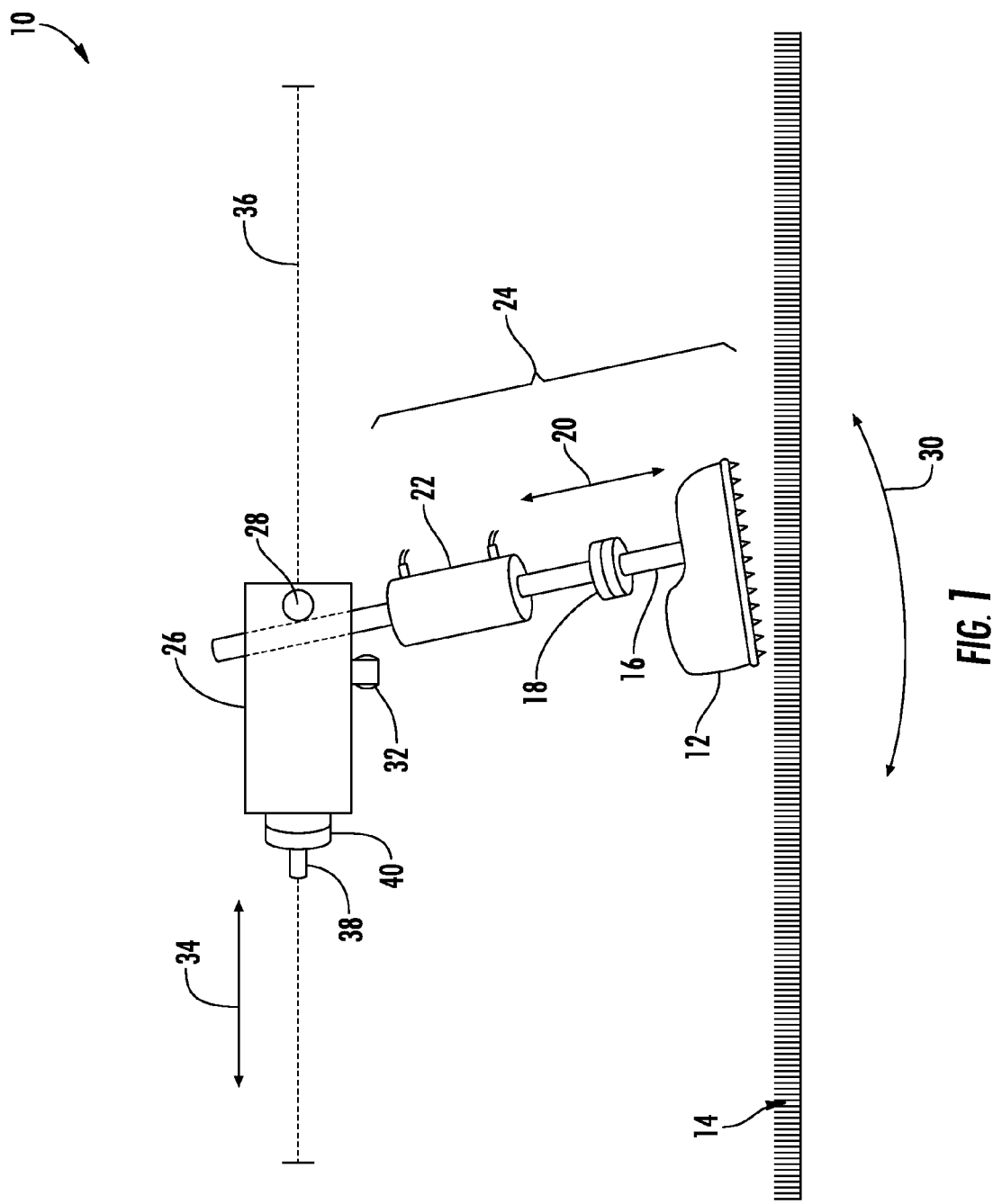
FIG. 1 schematically illustrates a non-limiting embodiment of a turf testing apparatus.

FIG. 1 schematically shows a first embodiment of a turf testing apparatus 10 for investigating forces related to the interface of a shoe 12 with a turf surface 14. Turf surface 14 may be any artificial or natural turf surface. Shoe 12 may be any type of footwear (including cleated and non-cleated footwear) or other construct for investigation (including, without limitation, a construct simulating a bare foot, an animal paw or hoof, or some other type of construct for investigation).

In this embodiment, although not shown in the Figures, the shoe 12 is mounted to a foot-form (for instance, a conventional shoe tree) allowing the shoe 12 to be securely associated with the apparatus 10, while also allowing the shoe 12 to be removed and interchanged with other footwear for testing.

The foot-form connects to the rest of apparatus 10 at connector 16. As shown, connector 16 connects to the foot-form/shoe 12 assembly towards the toe portion of the shoe 12, although the foot-form and/or connector 16 may be configured to connect the foot-form/shoe 12 assembly at other portions, including central portions of the shoe 12 and towards heel portions of the shoe 12.

Although not shown, connector 16 may include or be associated with one or more adjustment features allowing the position and/or orientation of the shoe 12 relative to the rest of the apparatus 10 to be adjusted. For instance, in some embodiments, the connector 16 may include one or more pivots for adjusting the rotational orientation of the shoe 12 relative to the turf surface 14. For instance, FIGS. 2A, B and C schematically illustrate shoe 12 (viewed from the front) at various states of rotation relative to the turf surface 14. In other embodiments, other portions and components of the apparatus 10 may be tilted at the same time to effect the various states of rotation shown in FIGS. 2A-C. In some embodiments, the foot-form/shoe 12 assembly may also be reversible such that the shoe 12 is mounted relative to the apparatus 10 with the heel portion at the front, rather than the toe portion being at the front as shown in FIG. 1.

The apparatus 10 shown in FIG. 1 includes a force sensor 18 for detecting forces along a substantially vertical axis 20. Force sensor 18 may be an inline compression load cell available from FUTEK Advanced Sensor Technology, Inc. of Irvine, Calif., or any other suitable force sensor. As shown in FIG. 1, the force sensor 18 is mounted inline between connector 16 and actuator 22, discussed below.

Actuator 22 is capable of moving shoe 12 along vertical axis 20, in both upward and downward directions. In one particular embodiment, actuator 22 is a double acting air cylinder having an up-stroke and down-stroke. Actuator 22 may be used to simulate a downward force of a body weight along substantially vertical axis 20. In embodiments where actuator 22 is an air cylinder, adjustment of air pressure may facilitate simulating different body weights (i.e. greater air pressure equates to greater body weight). Actuator 22 may also include functionality to adjust the speed of the up and down-strokes. In one embodiment in which actuator 22 is an air cylinder, a dump valve may maximize the speed of the down-stoke whereas a control valve may be used to regulate the speed of the up stroke. In other embodiments, the speed of both the up and down strokes may be adjustable/regulated.

Although not shown in FIG. 1, in some embodiments, it may be desirable to associate a supporting structure with one or more of the actuator 22, connector 16, and foot-form/shoe 12 assembly (referred to collectively as the "shoe sub-assembly 24" below). For instance, in some embodiments, actuation of actuator 22 may exert large forces on components of the shoe sub-assembly 24, such as a shaft of an air cylinder, potentially damaging these or other components of the apparatus 10. A supporting structure may increase the robustness of these components and help to protect against damage.

In the embodiment shown in FIG. 1, the shoe sub-assembly 24 is mounted to a carriage 26 at a pivot 28, which allows the shoe 12 to pivot along arc 30. In this particular embodiment, apparatus 10 is configured such that shoe 12 is initially at an approximately 11 degree angle relative to turf surface 14 (when viewed from the side, as in FIG. 1). As shown, the shoe-sub assembly 24 (particularly the upper shaft associated with actuator 22) is positioned slightly behind the associated pivot 28, such that the center of gravity of the shoe sub-assembly 24 will cause it to be initially biased at an approximately 11 degree angle. In some embodiments, the initial angle of shoe 12 may be adjustable, or may be pre-set for other angulations. The apparatus 10 shown in FIG. 1 also includes a stop 32 for limiting the amount the shoe sub-assembly 24 can pivot in a rearward direction. In some embodiments, stop 32 or other components may be adjustable to alter how far shoe sub-assembly 24 may pivot in the rearward direction.

In some embodiments, pivot 28 may be locked in a particular angular orientation such that the shoe sub-assembly 24 cannot pivot relative to carriage 26. In some embodiments, shoe sub-assembly 24 is fixed in position relative to carriage 26, and cannot pivot at all.

As mentioned above, in the embodiment of FIG. 1, shoe sub-assembly 24 is pivotally mounted to carriage 26. Carriage 26 may be driven along a substantially horizontal axis 34. An elongated track, schematically represented by dashed line 36, may extend generally along the substantially horizontal axis 34 to guide and support carriage 26.

Figure 2A:
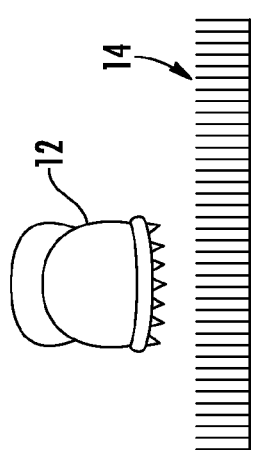
FIGS. 2A-C illustrate a shoe positioned in different orientations relative to a turf surface.
Figure 2B:
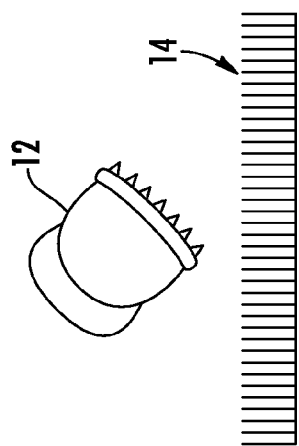
Figure 2C:
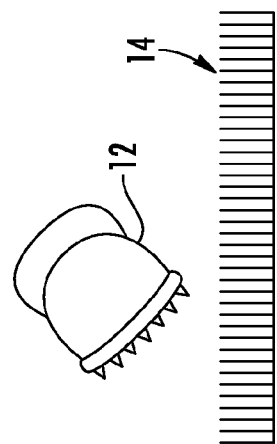

Elongated track 36 may in turn be supported by an external framework (shown in FIGS. 4-6) that rests on turf surface 14. In some embodiments, the elongated track 36 may be pivotally adjustable with respect to the external framework, which may be an additional or alternative mechanism for pivoting the shoe 12 with respect to turf surface 14 as shown in FIGS. 2A-C. In some embodiments, mobility of the entire apparatus 10 may be facilitated by deployable wheels or other suitable structure or functionality associated with the external framework.

Figure 4:
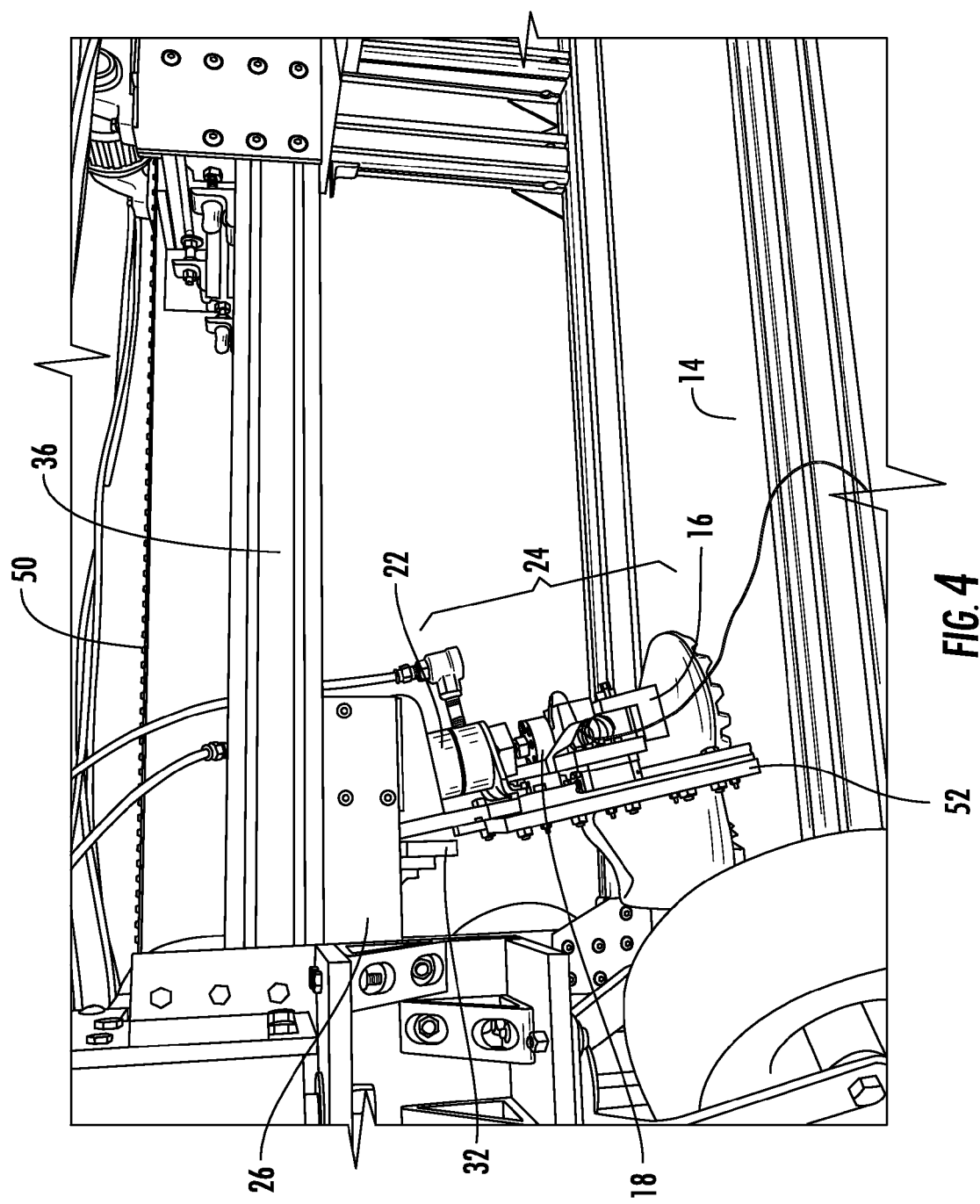
FIG. 4 is a perspective view of a portion of a turf testing apparatus according to one embodiment.

Carriage 26 may be driven along the elongated track 36 (along substantially horizontal axis 34) by another actuator. Although not shown in FIG. 1, in this particular embodiment, the actuator driving carriage 26 is a servo-driven belt drive 50 (FIG. 4). Carriage 26 connects to the belt of the drive at connector 38. In this particular embodiment, a second force sensor 40 is positioned in line with connector 38 and carriage 26, and is capable of measuring tension and/or compression forces along the substantially horizontal axis 34. One suitable, albeit non-limiting, example of a second force sensor 40 is a tension and compression load cell available from FUTEK Advanced Sensor Technology, Inc. of Irvine, Calif.

FIGS. 3A-D schematically illustrate a non-limiting example of an impaction and release cycle of shoe 12 and turf surface 14 using the turf testing apparatus 10 of FIG. 1. In FIG. 3A, shoe 12 (and its associated carriage 26 not shown in this Figure) is moving along a substantially horizontal axis at a constant velocity and at an angle (when viewed from the side) of approximately 11 degrees to the turf surface 14. FIG. 3B shows the shoe 12 and turf surface 14 just after the down-stroke of actuator 22 (not shown). In the particular configuration illustrated in this example, the heel of shoe 12 contacts turf surface 14 prior to the toe of shoe 12. FIG. 3C shows the shoe 12 now in full contact (both heel and toe) with turf surface 14. In this particular configuration, the carriage 26 (not shown) has continued at a constant velocity in the substantially horizontal direction while traction, friction and/or other interactions between the shoe 12 and turf surface 14 has at least slightly slowed the velocity of shoe 12 relative to carriage 26, resulting in shoe 12 pivoting about pivot 28 (not shown in this Figure) at least somewhat such that the shoe is in a vertical position. In certain configurations, depending on friction, traction and other characteristics of the turf surface 14 and/or shoe 12, as well as various settings of the apparatus 10, the shoe 12 may slip or slide at least somewhat relative to the turf surface 14 at this point. In certain configurations, as the carriage continues moving, the shoe 12 may continue to rotate such that only or primarily the toe of the shoe 12 is in contact with or otherwise engaged with the turf surface 14. FIG. 3D shows the shoe 12 and turf surface 14 just after the up-stroke of actuator 22.

Figure 6:
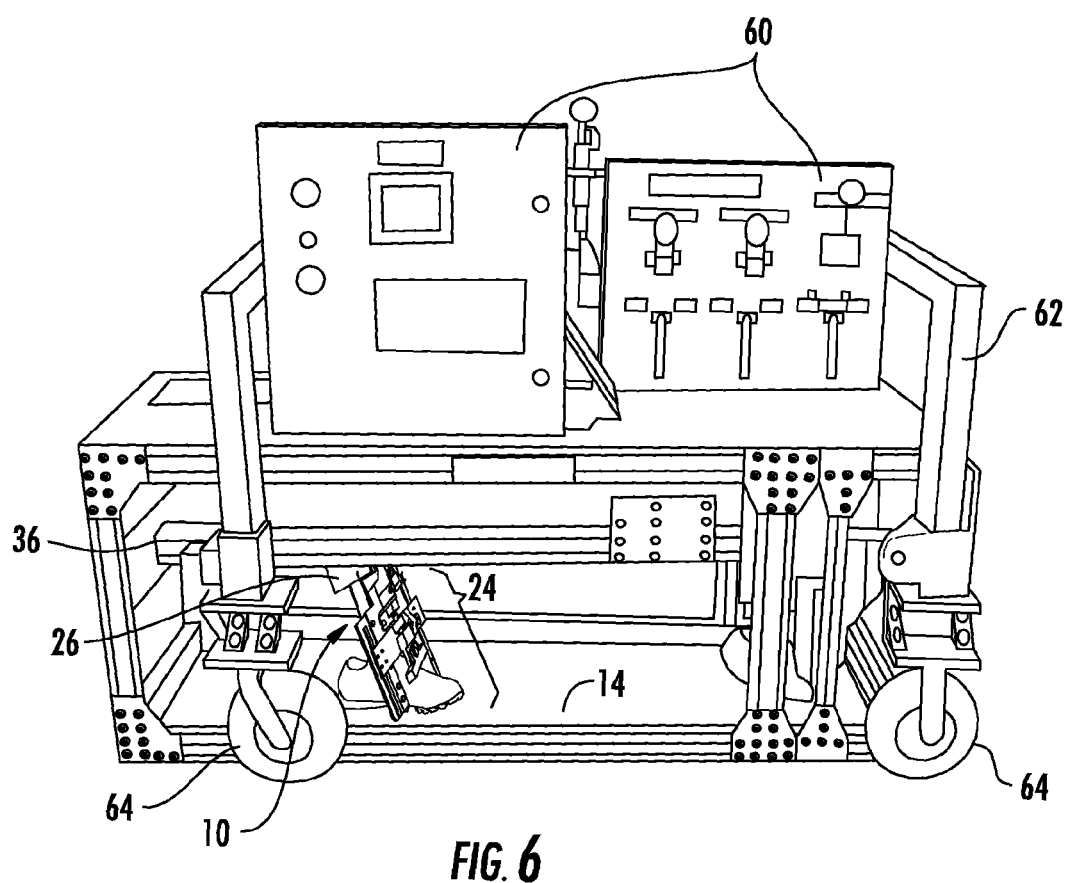
FIG. 6 is another perspective view of the apparatus shown in FIG. 4.

As shown in FIG. 6 and discussed in more detail below, the apparatus 10 of FIG. 1 may be associated with a monitoring and control system, which, in various embodiments, may be either a computer system, manual system or combination of computer and manual controls and monitoring functionality. In various embodiments, the monitoring and control system may allow adjustment and control of one or more of: (1) the speed of the second actuator (e.g. speed of a servo drive), which in turn will control the horizontal speed of the carriage 26 and shoe sub-assembly 24; (2) acceleration rate of the second actuator (e.g. rate at which the carriage accelerates to the set horizontal speed); (3) deceleration rate of the second actuator; (4) the horizontal position where the carriage will reach the set horizontal speed; (5) the horizontal position where the carriage will start to decelerate; (6) the horizontal position where the actuator 22 will move the shoe 12 into contact with the turf surface 14 (i.e. the downstroke position); (7) the horizontal position where the actuator 22 will move the shoe 12 away from the turf surface 14 (e.g. the upstroke position); and the pressure applied to the air cylinder of the actuator 22 (i.e. amount of force of the downstroke). In some embodiments, the monitoring and control system can cause the shoe 12 to contact and release from the turf surface 14 several times during a run.

The monitoring and control system, an example of which is shown in FIG. 6, may be used to monitor and record force readings from force sensors 18 and 40 (shown in FIG. 1) throughout or periodically during a run of the apparatus 10. The force readings may be recorded, for instance, as a function of force vs. distance traveled (e.g. horizontal position of the carriage 26), as a function of force vs. time, or in other manners. Data reflecting the force readings may be output as tables, charts, or in other manners.

The above described apparatus 10 and methods of using such apparatus 10 facilitate the study of various forces acting on/caused by the shoe/turf interaction during a simulated impact and release of the moving shoe from the turf surface. Different turf surfaces, including artificial and natural turf surfaces, may be studied, compared and contrasted. Such studies can include use of a wide variety of footwear, at different angles of impaction (in angular and normal planes to the turf surface), and at various simulated body weights and running speeds.

Figure 5:
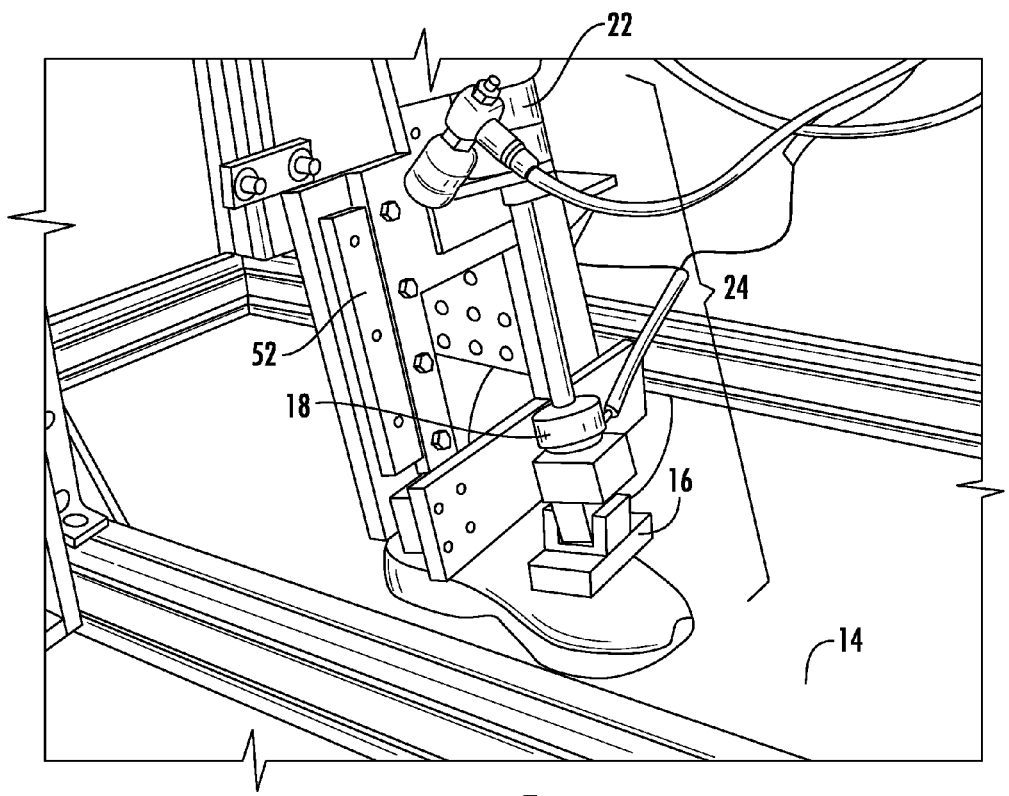
FIG. 5 is another perspective view of the apparatus shown in FIG. 4.

FIGS. 4 and 5 show an embodiment of the turf testing apparatus 10 as illustrated in FIG. 1. In FIG. 4 the shoe 12 is mounted to a foot-form (not shown in FIG. 4) allowing the shoe 12 to be securely associated with the apparatus 10, while also allowing the shoe 12 to be removed and interchanged with other footwear for testing. The foot-form connects to the rest of apparatus 10 at connector 16. The apparatus 10 shown in FIGS. 4 and 5 also includes a supporting structure 52 for reinforcing the shoe sub-assembly 24. As described above, the apparatus 10 shown may include a force sensor 18 for detecting force along a substantially vertical axis. As shown in FIG. 4, the force sensor 18 may be mounted inline between connector 16 and actuator 22. Actuator 22 is capable of moving shoe 12 along a vertical axis in both upward and downward directions as described above. A second force sensor (not shown in FIGS. 4 and 5) may be used for detecting force along a substantially horizontal axis. The shoe sub-assembly 24 may be mounted to a carriage 26 at a pivot (not shown in FIGS. 4 and 5), which allows the shoe 12 to pivot along an arc as described above. The carriage 26 is driven along a substantially horizontal, elongated track 36 by a servo-driven belt drive 50.

FIG. 6 illustrates various components associated with a monitoring and control system 60 associated with the assembly 10, which, in various embodiments, may be either a computer system, manual system or combination of computer and manual controls and monitoring functionality. The monitoring and control system 60 may monitor and record force readings from force sensors throughout or periodically during a run of the apparatus 10. The force readings may be recorded, for instance, as a function of force vs. distance traveled (e.g. horizontal position of the carriage 26), as a function of force vs. time, or in other manners. Data reflecting the force readings may be output as tables, charts, or in other manners. In the embodiment shown in FIG. 6, the entire apparatus 10 has an external framework 62 that rests on wheels 64, allowing the movement of the apparatus 10 with respect to the turf 14. As shown in FIG. 6, the external framework 62 also supports additional components of the apparatus not described above, such as the machinery, computers, and other components and that may be used to monitor and control the various components of the turf testing apparatus.

Additions, changes, deletions and other modifications may be made to the non-limiting embodiments described above without departing from the scope or spirit of the present invention. For instance and without limitation, embodiments of the turf testing apparatus described herein could be modified for testing things other than shoes, such as tires, medical prosthetics, or other structures or functional units that contact a surface while in motion. Additionally, it will be apparent to those of ordinary skill in the art that the testing apparatus described herein and similar apparatus may be used for testing surfaces other than turf surfaces, including various types of flooring, dirt surfaces, gravel surfaces, hard surfaces, soft surfaces or other surfaces, including surfaces in orientations other than horizontal surfaces, such as vertical and inclined surfaces.

The invention claimed is:

1. A turf testing apparatus comprising:
   a shoe;
   a first mechanically powered actuator coupled to the shoe, the first actuator configured to move the shoe along a horizontal axis;
   a second mechanically powered actuator coupled to the shoe for moving the shoe in both an upward and downward direction along a vertical axis relative to a surface; and
   a pivot configured to adjust the rotational orientation of the shoe relative to the surface;
   wherein the first actuator and second actuator cooperate to raise, lower, and horizontally move the shoe relative to the surface.

2. The turf testing apparatus of claim 1, wherein the first actuator is configured to move the shoe along the substantially horizontal axis without the shoe contacting the surface.

3. The turf testing apparatus of claim 2, wherein the second actuator is configured to move the shoe along the substantially vertical axis such that the shoe contacts the surface.

4. The turf testing apparatus of claim 3, wherein the first actuator is configured to continue to move the shoe along the substantially horizontal axis after the second actuator has moved the shoe into contact with the surface.

5. The turf testing apparatus of claim 4, wherein the pivot allows the shoe to pivot relative to the surface while the first actuator continues to move the shoe along the substantially horizontal axis while the shoe is in contact with the surface.

6. The turf testing apparatus of claim 5, wherein the second actuator is configured to move the shoe along the substantially vertical axis to move the shoe away from the surface.

7. The turf testing apparatus of claim 1, further comprising:
   a first force sensor and a second force sensor coupled to the shoe;
   wherein the first force sensor is configured to measure forces along the substantially horizontal axis during at least portions of the movement of the shoe; and
   wherein the second force sensor is configured to measure forces along the substantially vertical axis during at least portions of the movement of the shoe.

8. The turf testing apparatus of claim 7, wherein at least one of the force sensors is an inline compression load cell.

9. The turf testing apparatus of claim 1, further comprising a stop configured to prevent the shoe from pivoting past the stop.

10. The turf testing apparatus of claim 1, wherein the shoe is mounted to a carriage configured to be driven along the substantially horizontal axis.

11. The turf testing apparatus of claim 1, wherein the shoe is mounted to the carriage via the pivot.

12. A method of testing turf comprising:
actuating a mechanically powered first actuator to move a shoe in a substantially horizontal axis;
actuating a mechanically powered second actuator to move the shoe in a substantially vertical axis to bring the shoe in contact with a turf surface as the shoe moves along the substantially horizontal axis;
pivoting the shoe relative to the turf surface as the shoe moves along the substantially horizontal axis via a pivot;
moving the shoe along the substantially vertical axis to move the shoe away from the turf surface via the second actuator; and
measuring vertical and horizontal forces generated during at least a portion of the shoe's movement.

13. The method of claim 12, further comprising evaluating the measurements generated, adjusting a property of the turf surface based on the measurement, and manufacturing the turf surface to incorporate the adjusted property.

14. The method of claim 12, further comprising using a first force sensor to measure the horizontal force.

15. The method of claim 12, further comprising using a second force sensor to measure the vertical force.

16. The method of claim 12, further comprising analyzing the vertical and horizontal forces to reach conclusions about the turf surface.

17. The method of claim 12, further comprising using a monitoring and control system to adjust one or more of: (1) a speed of the second actuator; (2) an acceleration rate of the second actuator; and (3) a deceleration rate of the second actuator.

18. A surface testing apparatus comprising:
a mount configured to mount a foot;
a first mechanically powered actuator configured to move the mount along a first axis relative to a surface for testing;
a second mechanically powered actuator configured to move the mount along a second axis relative to the surface for testing, the second axis being transverse to the first axis;
a pivot configured to allow the mount to pivot relative to a third axis, the third axis being transverse to the first axis;
a first force sensor configured to sense forces along the first axis; and
a second force sensor configured to sense forces along the second axis.

19. The surface testing apparatus of claim 18, further comprising a frame configured to sit on the surface for testing in a substantially stationary condition during movement of the mount along the first and second axes.

20. The surface testing apparatus of claim 18, wherein the surface testing apparatus is configured to, at an initial position, orient the foot such that a lower surface of the foot is angled relative to the surface for testing, and, at an intermediate position, allow the foot to have pivoted such that the lower surface of the foot is substantially parallel to the surface for testing.

21. The surface testing apparatus of claim 18, wherein the surface testing apparatus is configured such that in use, the first axis is substantially horizontal to the surface for testing and the second axis is substantially vertical relative to the surface for testing.

22. The surface testing apparatus of claim 21, wherein the pivot is configured to, in use, allow the foot to pivot relative to the surface for testing while at least a portion of the foot is pressed against the surface for testing and while the first actuator is exerting a force on the foot along the first axis.

* * * * *